US006455526B1

(12) United States Patent
Kohn et al.

(10) Patent No.: US 6,455,526 B1
(45) Date of Patent: Sep. 24, 2002

(54) BIODEGRADABLE POLYMER ENCAPSULATED PHARMACEUTICAL COMPOSITIONS AND METHOD FOR PREPARING THE SAME

(75) Inventors: Rachel S. Kohn, Springfield, NJ (US); Stephen J. Hanley, Lebanon, NJ (US); Stephen J. Comiskey, Doylestown, PA (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/454,555

(22) Filed: Dec. 7, 1999

Related U.S. Application Data

(60) Provisional application No. 60/155,257, filed on Dec. 16, 1998.

(51) Int. Cl.[7] .................. A61K 31/495; A61K 31/50
(52) U.S. Cl. ...................................... 514/248
(58) Field of Search ........................ 424/426; 514/248

(56) References Cited

U.S. PATENT DOCUMENTS

| | | | |
|---|---|---|---|
| 4,389,330 A | 6/1983 | Tice et al. | |
| 4,801,460 A | 1/1989 | Goetz et al. | |
| 5,134,122 A | 7/1992 | Orsini | |
| 5,225,205 A | 7/1993 | Orsini | |
| 5,360,610 A | 11/1994 | Tice et al. | |
| 5,439,688 A | 8/1995 | Orsolini et al. | |
| 5,456,917 A | 10/1995 | Wise et al. | |
| 5,456,923 A | 10/1995 | Nakamichi et al. | |
| 5,505,963 A | 4/1996 | Münch et al. | |
| 6,239,143 B1 * | 5/2001 | Cain et al. | 514/307 |
| 6,277,864 B1 * | 8/2001 | Mondadori et al. | 514/317 |

FOREIGN PATENT DOCUMENTS

WO 9118602 * 12/1991

OTHER PUBLICATIONS

Journal of Controlled Release; 28 (1994) pp 121–129; Hiroaki Okada et al. "Drug delivery using biodegradable microspheres".

Pharmacy International; Dec. 1986; pp 316–318; J. Heller "Controlled drug release from monolithic bioerodible polymer devices".

* cited by examiner

*Primary Examiner*—Alton Pryor
(74) *Attorney, Agent, or Firm*—Balaram Gupta

(57) ABSTRACT

A new class of biodegradable pharmaceutical compositions useful as sustained release medicamentous compositions, including methods of making and methods of using these compositions, are described and claimed. The method of making these compositions include the steps of: a) dry mixing of a pharmaceutically active molecule with a biodegradable polymer; b) melt extruding the mixture to form a solid solution of the active molecule in the polymer; and c) pulverizing the solid solution to form microparticles such that they can be formed into injectable formulations. Preferred embodiments include pharmaceutical compositions of polylactide-co-glycolide and (+)-α-(2,3-dimethoxyphenyl)-1-[2-(4-fluorophenyl)ethyl]-4-piperidinemethanol (active ingredient) and a method for its formation. These compositions release the active ingredient at a steady rate over a period of days to weeks. The active ingredient antagonizes the effects of serotonin at the $5HT_{2A}$ receptor and are useful in treating various conditions such as, for example, psychoses including schizophrenia, obsessive compulsive disorder, sleep disorder, depression, anorexia, anxiety, drug addiction and bipolar disorders.

43 Claims, No Drawings

BIODEGRADABLE POLYMER ENCAPSULATED PHARMACEUTICAL COMPOSITIONS AND METHOD FOR PREPARING THE SAME

This application claims the priority of U.S. Provisional Application Ser. No. 60/155,257, filed Dec. 16, 1998.

BACKGROUND OF THE INVENTION

1. Field of the Invention

This invention relates to methods for the production of sustained release compositions containing a biodegradable polymer and a pharmaceutically active molecule, which are useful in the treatment of a variety of diseases, including certain psychoses such as, for example, schizophrenia, obsessive compulsive disorder, anxiety, and bipolar disorders. More specifically, the present invention relates to sustained release compositions of a biodegradable polyester and a pharmaceutically active molecule capable of exerting serotonin receptor antagonist activity at the $5HT_2$ receptor, method of making the same, and method of treating patients in need of such compositions.

2. Description of the Prior Art

It has long been appreciated that the continuous release of certain drugs over an extended period following a single administration could have significant practical advantages in clinical practice. It is also well recognized in the art that delivering a drug to its therapeutic site of action, such as, for example, the central nervous system (CNS) can be a very difficult task because of the numerous chemical and physical barriers which must be overcome in order for such delivery to be successful. A particularly difficult problem is in long term administration of a drug to patients suffering from CNS related diseases. This is particularly true for patients suffering from various CNS related diseases, such as schizophrenia, obsessive compulsive disorders, sleep disorders, depression, anxiety, anorexia and drug addiction. In addition, there is a need to maintain a steady drug level in patients suffering with these diseases so as to provide an improved efficacy in treatment with lower peak drug concentrations.

As a result, many methods have been developed to deliver drugs to the CNS effectively. One such method involves preparation of sustained release formulations. The sustained release formulations may however be of various different types. For example, a drug may be chemically modified into a form called a prodrug, that is capable of transforming into its active form slowly, either before or after crossing the blood-brain barrier. An example of such a prodrug delivery system consists of the neurotransmitter dopamine attached to a molecular mask derived from the fat-soluble vitamin niacin. The modified dopamine is taken up into the brain where it is then slowly stripped from its prodrug mask to yield free dopamine.

Other common methods used to prepare sustained release formulations include formation of microparticles in which bioactive agents are contained within a compatible biodegradable polymer. A number of methods are reported in the art, which use a wide range of organic solvents to prepare such microparticles. For example, U.S. Pat. No. 4,389,330 describes a method of forming microcapsules by dissolving or dispersing an active agent along with a wall forming material in a solvent. Common solvents used for the formation of such microcapsules include chlorinated hydrocarbons, particularly, methylene chloride, acetone, alcohols, and the like. However, due to environmental and toxicological considerations it is not possible to make certain of these drug formulations using solvents. Particularly, there are a number of regulatory restrictions in disposing of the solvent and solid wastes produced during the manufacture of these drug formulations.

In addition, there are many disadvantages to the solvent method of producing microparticle drug formulations. First, this method is uneconomical for an industrial size scale-up. Second, there are also quality concerns such as reproducibility and consistency of the drug distribution in the polymer matrix, thus causing serious regulatory compliance problems. Finally, the solvent method generally produces only the microspheres in powder form.

To overcome some of the problems of the solvent method of producing microparticles, there are methods known in the art to melt extrude a solid mixture of drug molecules and a variety of polymeric binders. For example, U.S. Pat. No. 5,439,688 describes a process for preparing a pharmaceutical composition for the sustained release of a drug molecule. However, all of the drug molecules described therein are synthetic or naturally occurring peptides. U.S. Pat. No. 5,456,923 describes a process for producing a solid dispersion of a drug dissolved or dispersed in a polymer or a diluent using a twin screw extruder. However, none of these prior art references teaches a formation of sustained release pharmaceutical compositions using a melt extrusion process wherein such compositions are suitable for the treatment of any of the CNS diseases described hereinabove. Furthermore, none of the prior art references describes a method for the formation of microparticles wherein the drug molecules are dissolved in the polymeric matrix and are useful in forming injectable formulations for the treatment of CNS related diseases.

The following references are disclosed as background.

U.S. Pat. No. 4,389,330 describes a microencapsulation process for the formation of microcapsules laden with an active agent involving a series of steps using a solvent.

U.S. Pat. No. 4,801,460 describes a process for the preparation of solid pharmaceutical forms by an injection molding or an extrusion process.

U.S. Pat. No. 5,360,610 describes polymeric microspheres as injectable, drug-delivery systems for use to deliver bioactive agents to sites within the central nervous system.

U.S. Pat. No. 5,439,688 and references cited therein describe processes for preparing pharmaceutical compositions for the sustained and/or controlled release of a drug using a biodegradable polymer and incorporating as the active substance the salts of a natural or synthetic peptide.

U.S. Pat. No. 5,456,917 describes a method for making an implantable bioerodible material for the sustained release of a medicament.

U.S. Pat. No. 5,456,923 describes a method of manufacturing solid dispersion in which a drug is dissolved or dispersed in a polymer carrier or a diluent. The solid dispersions are formed in a twin screw extruder.

U.S. Pat. No. 5,505,963 describes a method for making a pharmaceutical composition free of organic solvents useful for oral administration. The method employs a solidified granulates of an active ingredient in admixture with a meltable auxiliary substance which is soluble in the active ingredient at elevated temperatures.

J. Controlled Release, 28 (1994) 121–129 describes a review of drug delivery systems using various kinds of biodegradable polymers.

Pharmacy International, (1986), 7 (12), 316–18, describes a review of controlled drug release from monolithic bioerodible polymer devices.

All of the references cited herein are incorporated herein by reference in their entirety.

SUMMARY OF THE INVENTION

Accordingly, it is an object of the present invention to provide a melt extrusion method for the formation of microparticles in which the drug molecules are substantially dissolved in the polymer matrix forming a solid solution. It is further an object of the present invention to provide microparticles capable of releasing the drug molecules at a sustained release rate over an extended period of time. Finally, it is also an object of the present invention to provide injectable microparticle formulations for the treatment of various CNS diseases including diseases or conditions treatable by antagonizing the effects of serotonin at the $5HT_2$ receptor, such as schizophrenia, obsessive compulsive disorders, sleep disorders, depression, anxiety, anorexia and drug addiction.

Surprisingly, it has now been found that solid solution of a biodegradable polymer and a pharmaceutically active molecule can be made by a melt extrusion process. Some of the advantages gained by the practice of the method of the present invention, individually and/or in combinations, are: a) the pharmaceutically active compound is essentially dissolved in the biodegradable polymer matrix forming a solid solution; b) the compositions of the present invention can be readily formed into microparticles; and c) the compositions of the present invention can be formulated into injectable formulations for the sustained release of the active compound. Advantageously, the compositions of the present invention are useful in the treatment of various CNS diseases.

Thus, in accordance with the practice of the present invention there is provided a method for the production of a pharmaceutical composition comprising the steps of:
a) mixing a suitable amount of pharmaceutically active molecule capable of exerting serotonin receptor antagonist activity with a suitable amount of biodegradable polymer for a sufficient period of time and at suitable temperature and pressure conditions to form a dry mixture of said pharmaceutically active molecule and said polymer, wherein said biodegradable polymer has a glass transition temperature ($T_g$) of less than about 60° C.;
b) subjecting said dry mixture to a suitable shear mixing under suitable temperature and pressure conditions for a sufficient period of time such that said polymer softens to form a fluidized medium and said pharmaceutically active molecule is sufficiently, dissolved to form a solid solution having substantially homogeneously dispersed mixture of said pharmaceutically active molecule and said polymer, and said homogeneous mixture is formed into a strand;
c) pelletizing said strand; and
d) pulverizing said pellets to form sustained release microparticles of the biodegradable polymer and the pharmaceutical composition, wherein the microparticles are having a size distribution in the range of from about 10 to 200 μm such that the microparticles are suitable for forming an injectable formulation.

In one of the preferred embodiments, a biodegradable polyester is used as the matrix polymer to dissolve a pharmaceutically active molecule capable of exerting serotonin receptor antagonist activity. In this preferred embodiment, the sustained release microparticles are formed in a twin screw extruder. In a more preferred embodiment of this invention, the twin screw extruder is made up of at least one left handed element and the extrusion is carried out at a preferred temperature range of from about 95° C. to about 115° C.

In another preferred embodiment, a solid solution is formed using a polylactide-co-glycolide polymer (PLGA) and a pharmaceutically active compound of Formula I or pharmaceutically acceptable salts thereof. In this preferred embodiment, the dry blend of PLGA polymer and compound I was dried in a vacuum oven at a temperature of about 25° C.

Formula I

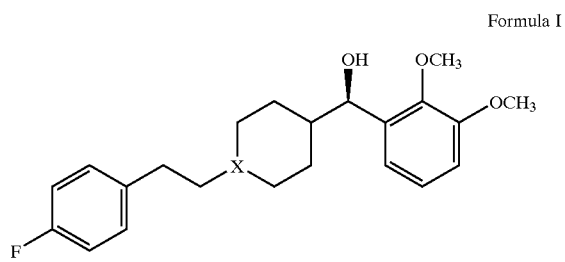

As such that the moisture content of the dry blend is less than about 0.02 weight percent. The melt extrusion of the dry blend was carried out in a twin screw extruder equipped with at least one left handed element to form a homogeneous mixture in which compound I is substantially dissolved in the PLGA matrix. In this preferred embodiment, pelletizing, pulverizing and sieving of the melt extruded blend affords microparticles having the size distribution of from about 10 to 100 μm, which are suitable for forming injectable formulations.

In another aspect of this invention, there is also provided a pharmaceutical composition for the sustained release of a medicamentous substance comprising microparticles having a size distribution in the range of from about 10 to 100 μm formed of:
a) a biodegradable polymer in an amount of about 80 to 95 percent by weight, wherein said polymer has a glass transition temperature ($T_g$) of less than about 60° C.; and
b) a pharmaceutically active compound of Formula I or a pharmaceutically acceptable salt thereof in an amount of about 5 to 20 percent by weight;

Formula I

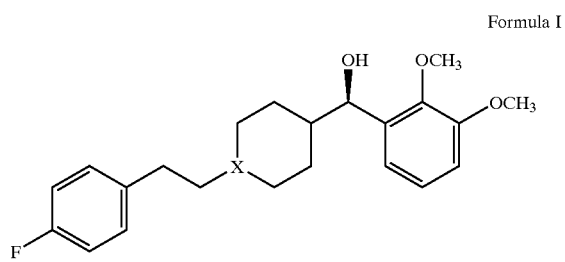

wherein said compound is substantially dissolved and uniformly dispersed in said polymer.

DETAILED DESCRIPTION OF THE INVENTION

As used herein the following terms shall have the assigned meanings and/or definitions:

"Biodegradable", "bioabsorbable", "bioresorbable" or "bioerodible" polymer shall mean any polymeric material capable of undergoing a degradation process in a biological environment, such as consumption by a human body and is converted to products that can be readily eliminated from the body.

"Drug", "medicament", "pharmaceutically active" or "therapeutically active" shall mean any organic compound or substance having bioactivity and adapted or used for a therapeutic purpose.

"Microparticles", "microspheres" or "microcapsules" shall mean any free flowing powder consisting substantially of spherical particles of 500 microns or less in diameter, usually 200 microns or less in diameter.

"Monolithic" shall mean a composition in which the active agent is substantially homogeneously dispersed throughout an essentially therapeutically inert matrix.

"Patient" means a warm blooded animal, such as for example rat, mice, dogs, cats, guinea pigs, and primates such as humans.

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicylic, hydroxyethanesulfonic, ethylenesulfonic, halobenzenesulfonic, toluenesulfonic, naphthalenesulfonic, methanesulfonic, sulfanilic, and the like.

"Pharmaceutically acceptable carrier" is a solvent, dispersant, excipient, adjuvant or other material having acceptable toxicity, which is mixed with the composition of the present invention in order to permit the formation of a pharmaceutical composition, i.e., a dosage form capable of administration to the patient. One example of such a carrier is a pharmaceutically acceptable oil typically used for parenteral administration.

"Solid solution" means that the pharmaceutically active molecule is substantially dissolved in the polymer to form a single phase system.

"Sustained release" means that a composition when administered to a patient is capable of releasing the active molecule at a steady rate for a period of at least 2 weeks, preferably for a period of about 2 weeks to one month or for longer periods if needed.

"Therapeutically effective amount" means an amount of the compound which is effective in treating the named disorder or condition.

"Treat" or "treating" means to alleviate symptoms, eliminate the cause of the symptom either on a temporary or permanent basis, or to prevent or slow the appearance of symptoms of the named disorder or condition.

One of the advantages of the present method of the invention is that the microparticles of well defined size distribution can be obtained in which the pharmaceutically active molecule is dissolved in the biodegradable polymer matrix forming a solid solution. This is achieved by a scalable melt extrusion process, thus avoiding the use of undesirable solvents as used by the conventional processes. Thus, the method of the present invention not only offers environmental benefits (i.e., avoids disposal of the solvents) but also provides an economical way of making sustained release drug formulations. Another important advantage of the method of the present invention is that the well defined microparticles of narrow; size distribution can be made by the practice of this invention, which are useful for forming a variety of injectable formulations. Yet another advantage gained by the practice of this invention is that solid solution of a biodegradable polymer and a pharmaceutically active molecule can be readily made wherein the active molecule is a neuro-active, non-peptidic small molecule and may contain a reactive group such as hydroxy group.

By judicious practice of the method of the present invention the microparticles formed are substantially free from any other reactive products of the pharmaceutically active molecule and the biodegradable polymer. Surprisingly, the method of the present invention offers pharmaceutical compositions in which the bioavailability of the pharmaceutically active molecule is enhanced because of the fact that the active molecule is substantially dissolved in the polymer matrix. Thus, the microparticles of the composition of the present invention are substantially "monolithic." That is, the active molecule is dispersed uniformly throughout the polymer matrix. It should be noted that many of these features described herein are not readily attainable by most of the conventional methods, including solvent and other melt extrusion methods.

In accordance with the practice of the present invention there is provided a method for the production of pharmaceutical compositions. In the method of the present invention, the first step involves mixing of a suitable amount of the pharmaceutically active molecule with a suitable amount of the biodegradable polymer for a sufficient period of time and at suitable temperature and pressure conditions to form a dry mixture.

Mixing of the polymer and the pharmaceutically active molecule can be done at ambient atmospheric conditions, preferably in the temperature range of from about 20° C. to 30° C. and at atmospheric pressure. The time required for mixing depends upon the quantities of the polymer and the active molecules used and may involve 30 minutes to 2 hours or longer. The polymer and the pharmaceutically active molecule may be used as received from the commercial sources, generally, in the form of powder or pellets. However, it has been observed that it is beneficial to grind the powder or pellets to form a well mixed dry mixture. Any of the grinding or milling techniques known in the art may be used for this purpose including cryogenic grinding or milling methods.

It has also been observed that drying of the dry mixture of polymer and pharmaceutically active molecule is also beneficial to remove any residual moisture in the polymer or the active molecule. Among several benefits, two key benefits of drying the dry mixture are: a) minimization of the degradation of the polymer; and b) minimization of any potential reaction between the polymer and the pharmaceutically active molecule. Any of the drying techniques known in the art may be used. For example, drying the mixture under vacuum at about room temperature, i.e., 20 to 30° C. for a period of about 2 to 48 hours or longer provides desirable results.

As stated hereinabove, a wide variety of non-peptidic pharmaceutically active molecules having a molecular weight less than about 600 may be used in this invention. The expression "non-peptidic" as used herein shall mean that the molecules which are not peptides, that is, molecules that are not formed by the reaction of two or more of the naturally occurring amino acids. A wide variety of biodegradable polymers may be employed in this invention, however, biodegradable polymers having a glass transition temperature ($T_g$) less than about 60° C. are particularly preferred. As used herein "glass transition temperature" refers to the softening temperature of the polymer, i.e., the transition temperature above which a noncrystalline polymer has enough thermal energy for long segments of each polymer chain to move randomly. In other words, at a temperature higher than the glass transition temperature, the polymer molecules have enough motion to be mobile, and this is referred to herein as a "fluidized medium."

In a second step of the method of the present invention the dry mixture as obtained in the first step is subjected to a suitable shear mixing at suitable temperature and pressure conditions for a sufficient period of time such that the polymer softens to form a fluidized medium. As used herein "shear mixing" means that mixing of the dry mixture at an elevated temperature, preferably above the glass transition temperature of the polymer, under shear using any of the methods known in the art. Preferably, shear mixing is carried out in a mixing bowl or an extrusion equipment as described herein. The conditions are maintained such that the pharmaceutically active molecule is allowed to dissolve in the fluidized polymer medium and form substantially a homogeneous mixture of the pharmaceutically active molecule and the polymer.

To obtain best benefits from this invention, it is critical that the pharmaceutically active molecule is sufficiently miscible or dissolved in the polymer matrix, as mentioned hereinabove. To determine the extent of pharmaceutically active molecule dissolved in the polymer matrix, a variety of techniques well known in the art may be used depending upon the type of polymer and the active molecule employed. In general, differential scanning calorimetry (DSC) may be used to determine the level of active molecule dissolved in the polymer if the active molecule has a definitive melting point. From the heat of fusion determined from the melting point peak of the active molecule, it is possible to compute the extent of active molecule dissolved. Thus, as more active molecule dissolves in the polymer the size of the melting peak is reduced correspondingly. The melting peak is completely absent when all of the active molecule is dissolved in the polymer. In addition, the glass transition temperature ($T_g$) of the polymer decreases with increasing solubility of the active molecule. Other techniques, such as scanning electron microscopy (SEM) may also be used to determine the homogeneity of the pharmaceutical composition of the present invention. That is, the undissolved pharmaceutically active molecule will appear as a separate phase.

In a third step of the method of the present invention, the fluidized mixture of the polymer and pharmaceutically active molecule is cooled to form a strand and pelletized. As used herein "pelletizing" refers to the formation of pellets from the strand formed according to this invention. Any of the well known methods in the art may be used to strand and pelletize the mixture of the polymer and pharmaceutically active molecule. For example, the molten fluid may by extruded into a strand by passing through an orifice. Then the strand is taken over a conveyor belt, which is being purged by dry nitrogen or air. The strand is finally fed into a pelletizer to form pellets.

In a final step, the pellets from the third step are pulverized to form sustained release microparticles of the biodegradable polymer and the pharmaceutically active molecule. As used herein "pulverizing" refers to conversion of pellets formed according to this invention to small particulate form using any of the known methods in the art to form the microparticles of this invention, such as cryogenic milling as described herein. The microparticles so formed are sieved such that they exhibit a size distribution in the range of from about 10 to 200 $\mu$m, more preferably 10 to 100 $\mu$m. These microparticles are suitable for forming an injectable formulation.

As discussed hereinabove, preferred pharmaceutically active molecules for the practice of the method of present invention are neuro-active molecules or agents. Examples of neuro-active molecules or agents that may be microencapsulated and used according to the present invention are neurotransmitters and neurotrophic factors including such agents as norepinephrine, epinephrine, serotonin, dopamine, substance P, somatostatin, and agonists and antagonists of these active molecules or agents.

Preferred pharmaceutically active molecules are those which are capable of exerting serotonin receptor antagonist activity. Particularly preferred pharmaceutically active molecules for the practice of the method of present invention are $5HT_{2A}$ receptor antagonists. A most preferred pharmaceutically active molecule is (+)-isomer of α-(2,3-dimethoxyphenyl)-1[2-(4-fluorophenyl)ethyl]-4-piperidinemethanol, Compound of Formula I or a pharmaceutically acceptable salt thereof.

Formula I

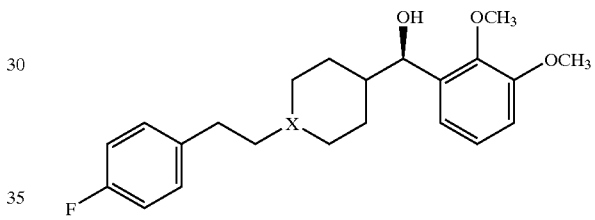

Any of the known biodegradable polymer may be used under certain specific conditions as described herein. For instance, a polymer having a glass transition temperature lower than 60° C. may be employed in the formation of microparticles of the present invention, provided that the pharmaceutically active molecules of the present invention are dissolved sufficiently in such a polymer matrix by practicing the method of the present invention. It should further be noted that such biodegradable polymer is suitable as a raw material in the manufacture of pharmaceutical products and its function is not adversely affected by the shear mixing step (i.e., step b) of the method of the present invention. Examples of such polymers are polyesters, polyamides, polyanhydrides, polyorthoesters, polycarbonates, poly(phosphoesters), poly(phosphazenes), poly(iminocarbonates), and the like. It should be noted that a mixture containing one or more of these polymers may also be employed. Such polymers are easily prepared as described in the literature cited herein and they can be obtained commercially from specialized firms known to those of ordinary skill in the pertinent manufacturing art.

Particularly preferred polymers suitable for the method of the present invention are polyesters. Specific examples of polyesters include polylactide, polyglycolide, polylactide-co-glycolide, polyhydroxybutyrate, polycaprolactone, polytartarate, and the like. Two or more mixtures of these polymers may also be used. A particularly preferred polyester is polylactide-co-glycolide (PLGA).

The PLGA polymer has a number of advantages which render it unique to the method of the present invention. An advantage of PLGA is that it is similar to materials used in the manufacture of present day bioabsorbable sutures. Another advantage is that this material is biocompatible with the tissue of the CNS. Still another advantage is that this material is biodegradable within the tissues of the CNS without producing any toxic byproducts of degradation.

An important advantage of this material, as it relates to this invention, is the ability to modify the duration of drug release by manipulating the polymer's biodegradation kinetics, i.e., by modifying the ratio of lactide and glycolide in the polymer. This is particularly important because the ability to deliver neuro-active molecules at a controlled rate over a predetermined period of time is a more effective and desirable therapy over current procedures for administration. Microparticles made with this polymer serve two functions: they protect drugs from degradation and they release drugs at a controlled rate over a predesired time. As stated hereinabove, although polymers have been previously reported for use in the microencapsulation of drugs including PLGA, the physical, chemical and medical parameters of the microencapsulating polymer for pharmaceutically active molecules to be used in accordance with the present invention are narrow. This is especially true for the formation of sustained release injectable pharmaceutical compositions for delivering to the CNS active drugs according to the present invention.

For instance, the PLGA polymer that is suitable in the method of the present invention may have a wide range of average molecular weight provided that its glass transition temperature is less than 60° C. However, preferably, the average molecular weight of PLGA polymer is in the range of from about 20,000 to about 100,000, and is more preferably between about 30,000 and 45,000. The PLGA polymer further contains 45 to 90 mole percent of lactide and 10 to 55 mole percent of glycolide units respectively.

Dry mixing of the polymer and the pharmaceutically active molecule in step (a) is conducted at ambient temperature, i.e., at around the atmospheric temperature and pressure conditions. More preferably, the dry mixing is carried out at a temperature in the range of about 20° C. to about 30° C. at atmospheric pressure conditions.

The shear mixing of the dry mixture in step (b) of the method of the present invention may be carried out using a variety of techniques known in the art. For example, mixing bowl equipped with a heating element and mixing blades may be used. Several different types of mixing bowls are available from commercial sources. Another preferred method of carrying out the shear mixing is by an extruder. Both single screw as well as twin screw extruders may be employed to carry out the shear mixing in step (b) of the method of the present invention. The twin screw extruder is particularly preferred.

The twin screw extruder is preferably a forward discharge extruder pelletizer characterized by the use of a couple of screws, which differentiate the machine from the single screw extruder. The single screw extruder has a single screw and often uses a prefabricated screw, and thus screw elements can not be varied as in the twin screw extruder as described further below.

To be more specific, the twin screw extruder comprises a metering feeder unit, a barrel (cylinder), screws, paddle means, screw shafts, barrel heater-cooler means, exit dies (cooling die, heating die, molding die) and extrudate cutter and provides for a free variation of compounding pressure and temperature through a choice of screw geometry, rotational speed, and screw elements to be mounted on the screw shafts. Furthermore, if necessary, the barrel can be used in a variety of combinations of length and type according to the intended use and its temperature can also be controlled as desired.

Thus, the twin screw extruder processes the feed with two screws and provides for change of the combination of axial screw elements so that it has many definitive advantages over the single screw extruder, namely:

(1) Compared with the single screw extruder, the twin screw extruder features positive conveying of materials between screws, which allows for easier compounding of shear sensitive or low viscosity materials. Thus, for example, mixing of dissimilar materials, such as oil and water, can be done better with a twin screw extruder.

(2) Also, compared with the single screw extruder, the twin screw extruder is by far superior in shear force, compounding effect and transport capacity.

Furthermore, it should be noted that judicious selection of the screw elements is extremely critical to obtain desired intended benefit from the practice of the method of the present invention. It is believed that the appropriate selection of the screw elements can affect the extent of solubility of the pharmaceutically active molecule in the polymer matrix. The screw elements further affect the homogeneity of the pharmaceutical composition. For example, it has been observed that the use of one or more of left handed elements minimizes the polymer degradation and increases the solubility of the pharmaceutically active molecule in the polymer matrix. In addition, it has been observed that proper selection of kneading elements further improves the uniform mixing and solubility of the pharmaceutically active molecule in the polymer matrix.

The processing parameters such as pressure, temperature, feed rate of polymer and the pharmaceutically active molecule, and amounts and feed rates of additives, if used any, are dependent on the type of pharmaceutically active molecule and of polymer, and the shear mixing equipment used. But it is important to select a combination of parameters such that the pharmaceutically active molecule, polymer, etc. will be maintained at temperatures below their decomposition points and vary the operating parameters according to the desired characteristics of the products. Thus, it is critical that the glass transition temperature ($T_g$) of the polymer used herein is preferably below 60° C. such that the shear mixing can be carried out at moderate temperatures as described below.

In general, shear mixing in step (b) is carried out at a temperature in the range of about 60° C. to about 140° C., preferably from about 80° C. to about 120° C., and more preferably from about 95° C. to about 115° C.

The compounding weight ratio of the pharmaceutically active molecule to the polymer is varied depending upon the type of pharmaceutically active molecule, polymer, and the intended use of the pharmaceutical composition. Preferably, the weight ratio of the pharmaceutically active molecule and the polymer is in the range of from about 5:95 to about 25:75, more preferably from about 10:90 to about 20:80, and most preferably from about 10:90 to about 15:85.

As stated hereinabove, an important benefit obtained from the practice of the present invention is that the pharmaceutically active molecule is sufficiently dissolved in the polymer matrix. The extent of pharmaceutically active molecule dissolved in the polymer matrix is controlled depending upon the intended end use and intended rate of release of the pharmaceutically active molecule. Preferably, at least 50 weight percent of the pharmaceutically active molecule is dissolved in the polymer, more preferably the pharmaceutically active molecule is dissolved in the polymer at least to an extent of about 90 weight percent, based on the total weight of the pharmaceutically active molecule present in the pharmaceutical composition.

As stated hereinabove, the pharmaceutical compositions in the form of microparticles are particularly suitable in injectable formulations, that is, in parenteral administration. For parenteral administration, the microparticles may be dispersed and/or dissolved in a physiologically acceptable pharmaceutical carrier and administered as either a suspension or solution. Illustrative of suitable pharmaceutical carriers are water, saline, dextrose solutions, fructose solutions, ethanol, or oils of animal, vegetable or synthetic origin. The pharmaceutical carrier may also contain preservatives, such as benzyl alcohol, buffers, etc., as are known in the art. Some oils which may be used for intramuscular injection are sesame, olive, arachnis, maize, almond, cottonseed, peanut and castor oil, with sesame oil being preferred. The sustained release formulation is preferably administered intramuscularly, subcutaneously or intravenously with intramuscular administration preferred although other routes of administration such as oral, transdermal, nasal spray, etc. could be used if appropriate to the needs of the patient.

The microparticles may be admixed with any inert carrier and utilized in laboratory assays in order to determine the concentration of the pharmaceutically active molecule released from the microparticles including the urine, serum, etc. of the patients as is known in the art.

Accordingly, the suspension or solution formed in accordance with the method of the present invention when administered to a patient releases the pharmaceutically active molecule for a period of at least about 2 weeks at a dose sufficient to antagonize the effects of serotonin at the $5HT_{2A}$ receptor, more preferably for a period of from about 2 weeks to about one month. However, suspension or solution capable of releasing the active molecule longer than one month may also be prepared if there is a need to administer such a suspension or solution to a patient in need thereof.

In one of the preferred embodiments, there is provided a method for the production of pharmaceutical composition, which comprises the following steps.

In step (a) of this preferred embodiment, suitable amount of pharmaceutically active molecule capable of exerting serotonin receptor antagonist activity is mixed with a suitable amount of biodegradable polyester for a sufficient period of time and at a temperature in the range of from about 20° C. to 30° C. and at atmospheric pressure conditions to form a well mixed dry mixture of the pharmaceutically active molecule and the polyester. Any of the polyesters described hereinabove may be used in this embodiment. As described hereinabove, the polyester should have a glass transition temperature ($T_g$) of less than about 60° C.

In step (b) of this preferred embodiment, the dry mixture from step (a) is fed into a twin screw extruder equipped with suitable kneading and mixing elements at suitable temperature and pressure conditions for a sufficient period of time such that said polymer softens to form a fluidized medium and at least 50 weight percent of the pharmaceutically active molecule is dissolved in the fluidized polyester medium to form a substantially homogeneously dispersed mixture of the pharmaceutically active molecule and the polyester. The homogeneous mixture is then formed into a strand as described hereinabove.

In a more preferred form of this embodiment it has been observed that utilization of at least one left handed element in building the screw remarkably improves the quality of the microparticles that are formed. The microparticles of this embodiment feature more of the pharmaceutically active molecule dissolved in the polyester matrix, and thus are more homogeneous. In addition, it has been observed that use of a narrow temperature range of about 95° C. to about 115° C., further improves the quality of the pharmaceutical compositions.

In step (c) of this preferred embodiment the strand of pharmaceutical compositions from step (b) is pelletized as described hereinabove.

Finally, in step (d) of this preferred embodiment, the pellets are pulverized to form an injectable sustained release microparticles of the pharmaceutical composition as described herein. The microparticles are then sieved to form uniform microparticles having a size distribution in the range of from about 10 to 200 µm.

In yet another preferred embodiment of the method of the present invention the solid solution containing the PLGA polymer and Compound I are formed as described hereinabove. In this preferred embodiment, the dry blending or mixing of PLGA and Compound I is conducted at a temperature of about 25° C. Preferred weight ratio of PLGA to Compound I is in the range of from about 10:90 to 15:85. In this embodiment, it has been observed that drying of the dry mixture under vacuum at a temperature of about 25° C. for a period of about 16 hours improves the quality of the microparticles. Particularly, it is beneficial to dry the mixture to such an extent that the moisture content of the mixture is less than about 0.02 weight percent. The moisture content of the dry mixture may be determined by any of the techniques known in the art, such as, for example, Karl Fisher Method. Drying minimizes any degradation of the PLGA polymer and substantially reduces the formation of any transesterification product between PLGA and Compound I.

In yet another facet of this invention there is also provided a pharmaceutical composition for the sustained release of a medicamentous substance comprising microparticles having a size distribution in the range of from about 10 to 100 µm formed of:

a) a biodegradable polymer, as described hereinabove, in an amount of about 80 to 95 percent by weight, wherein the polymer has a glass transition temperature ($T_g$) of less than about 60° C.; and b) a pharmaceutically active Compound I, as described herein, or a pharmaceutically acceptable salt thereof in an amount of about 5 to 20 percent by weight; wherein Compound I is substantially dissolved and uniformly dispersed in the PLGA matrix.

In a more preferred embodiment of this aspect of the invention, the preferred polymer is polylactide-co-glycolide polymer (PLGA). The preferred weight ratio of Compound I to PLGA is 15:85 to 5:95.

As described herein, the compositions of the present invention may be mixed with a pharmaceutically acceptable carrier capable of being administered by the preferred route in order to produce a sustained release of Compound I. That is (+)-α-(2,3-dimethoxyphenyl)-1-[2-(4-fluorophenyl) ethyl]-4-piperidinemethanol, Formula I can be supplied to the patient over a period of days or weeks. Preferably the sustained release formulation comprises microparticles of the present invention and a pharmaceutically acceptable carrier for parenteral administration as an aqueous suspension, oil solution, oil suspension or emulsion as described hereinabove. More preferably pharmaceutical compositions of the present invention when administered to a patient releases Compound I for a period of at least about 2 weeks, and most preferably for a period of from about 2 weeks to about one month at a dose sufficient to antagonize the effects of serotonin at the 5HT$_{2A}$ receptor.

Since the microparticles of the present invention release (+)-α-(2,3-dimethoxyphenyl)-1-[2-(4-fluorophenyl)ethyl]-4-piperidinemethanol ("Active Ingredient") into the patient for the therapeutic effect, the microparticles of the present invention are useful for all indications of use for which the Active Ingredient is useful. Some of these indications of use have been described in the patents issued generically encompassing the Active Ingredient (U.S. Pat. No. 4,783,471) or specifically covering the Active Ingredient (U.S. Pat. Nos. 5,134,149; 5,561,144; 5,618,824; 5,700,812; 5,700,813; 5,721,249; and PCT/US97/02597), all incorporated herein by reference. These references disclose uses of psychosis (including schizophrenia), obsessive compulsive disorder, thrombotic illness, coronary vasospasm, intermittent claudication, anorexia nervosa, Raynaud's phenomenon, fibromyalgia, extra-pyramidal side effects, anxiety, arrhythmia, depression and bipolar disorder, sleep disorder or drug abuse (e.g., cocaine, nicotine, etc.). Some of these indications have been disclosed in the patents described above and in U.S. Pat. Nos. 4,877,798; and 5,021,428; all incorporated herein by reference.

Psychoses as used herein are conditions where the patient experiences a major mental disorder of organic and/or emotional origin characterized by derangement of the personality and loss of contact with reality, often with delusions, hallucinations or illusions. Representative examples of psychotic illnesses which can be treated with the compositions of the present invention include schizophrenia, schizophreniform disorder, schizoaffective disorder, delusional disorder, brief psychotic disorder, shared psychotic disorder, psychotic disorder not otherwise specified, and substance-induced psychotic disorder. See Diagnostic and Statistical Manual of Mental Disorders, 4th ed., American Psychiatric Association, incorporated herein by reference. The Active Ingredient is currently in clinical trials for the treatment of schizophrenia.

The Active Ingredient has the profile of an atypical antipsychotic in numerous preclinical neurochemical, electrophysiological and behavioral models of antipsychotic activity. These effects include reduction of MDMA-induced dopamine release in the striatum, selective effects on A10 vs. A9 neuronal activity after chronic administration, blockade of amphetamine-stimulated locomotion, and reversal of 5-HT$_2$ agonist-induced deficits in prepulse inhibition and latent inhibition. See *Journal of Pharmacology and Experimental Therapeutics,* 266: 684–691 (1993), S. M. Sorensen et al., "Characterization of the 5-HT$_2$ receptor antagonist MDL 100,907 as a putative atypical antipsychotic: behavioral, electrophysiological and neurochemical studies"; *Journal Pharmacology and Experimental Therapeutics,* 277: 968–981 (1996), J. H. Kehne, "Preclinical characterization of the potential of the putative atypical antipsychotic MDL 100,907 as potent 5-HT$_{2A}$ antagonist with a favorable CNS safety profile"; and *CNS Drug Reviews,* 3(1): 49–67 (1997), C. J. Schmidt et al., "MDL 100,907: A selective 5-HT$_{2A}$ receptor antagonist for the treatment of schizophrenia"; all of these references are incorporated herein by reference.

Patients with obsessive-compulsive disorders (OCD) fail to inhibit or "gate" intrusive, distressing thought or images. Since OCD is characterized by deficient "cognitive gating" and by aberrant metabolic activity in circuitry linking the orbital cortex and straitum, it has been predicted that OCD patients might exhibit deficient PPI (prepulse inhibition). The Active Ingredient has been found to restore disrupted PPI. See *Psychopharmacology* 124: 107–116 (1996), R. A. Padich, et al., "5HT modulation of auditory and visual sensorimotor gating: II. Effects of 5HT$_{2A}$ antagonist MDL 100,907 on disruption of sound and light prepulse inhibition produced by 5HT agonists in Wistar rats."

The Active Ingredient is also effective in the prevention of acute thrombosis, especially those of the coronary arteries. This compound decreases the rate at which platelets aggregate as the result of minor alterations in the endothelial lining of the vasculature and therefore prevents the formation of acute pathological thrombi. See U.S. Pat. No. 5,561,144 for description.

Anxiety, variant angina, anorexia nervosa, Raynaud's phenomenon and coronary vasospams are used in the manner defined in the 27th edition of Dorland's Illustrated Medical Dictionary, incorporated herein by reference.

Fibromyalgia is a chronic disease state wherein the patient suffers from numerous symptoms such as, for example, widespread generalized musculoskeletal pains, aching, fatigue, morning stiffness and a sleep disturbance which can be characterized as inadequacy of stage 4 sleep.

Extra-pyramidal side effects often accompany the administration of neuroleptic agents such as haloperidol and chlorpromazine. Patients often experience a parkinsonian-like syndrome, wherein they experience muscular rigidity and tremors. Others experience akathisia and acute dystonic reactions.

The Active Ingredient increases the duration of the action potential of myocardial tissue producing an increase in the refractory period of that tissue, which under the classification system of Vaughan Williams, exhibits Class III anti-arrhythmic activity.

The pharmaceutical composition of the present invention may be used to treat drug abuse in the patient. See T. F. Meert, et al., *European Journal of Pharmacology* 183: 1924 where 5HT$_2$ antagonist abolished preference for both alcohol and cocaine in the rodent model of the drug abuse. Other animal models such as the rodent self-stimulation model described in R. A. Frank, et. al., *Behavioral Neuroscience* 101: 546–559 (1987) may be used to demonstrate the ability of the sustained release compositions of the present invention to treat drug abuse.

The compositions of the present invention are useful in treating patients with depressive disorders and bipolar disorders. In the Diagnostic and Statistical Manual of Mental Disorders (Third Edition-Revised) ("DSM-III-R"), incorporated herein by reference, depressive disorders are defined as major depression, dysthymia and depressive disorder NOS. We also include in this category major depressive episode including chronic type, melancholia, and seasonal pattern. Bipolar disorders include bipolar disorder, cyclothymia and bipolar disorder NOS.

A feature of depressive disorders is one or more periods of depression without a history of either manic or hypomanic episodes. A feature of bipolar disorders is the presence of one or more manic or hypomanic episodes usually accompanied by one or more major depressive episodes. A manic or hypomanic episode is a distinct period during which the predominant mood is either elevated, expansive or irritable and there are associated symptoms of the manic syndrome as defined in DSM-III-R. The disturbance is severe enough to cause marked impairment in occupational or social functioning.

Major depression has one or more major depressive episodes. A major depressive episode is characterized by: (1) at least five of the following: depressed mood, loss of interest in pleasure (anhedonia), significant weight loss or weight gain when not dieting, insomnia or hypersomnia, psychomotor agitation or retardation, fatigue or loss of energy, feelings of worthlessness or excessive or inappropriate guilt, diminished ability to think or concentrate, or recurrent thoughts of death including suicide; (2) it cannot be established that an organic factor initiated and maintained the disturbance; (3) there are no delusions or hallucinations for as long as two weeks in the absence of prominent mood symptoms; and (4) it is not superimposed on schizophrenia, schizophreniform disorder, delusional disorder, or psychotic disorder NOS.

Dysthymia has a history of a depressed mood more days than not for at least two years and during the first two years of the disturbance; the condition does not meet the criteria for a major depressive episode. The depressed mood in children and adolescents can be exhibited as irritability. Also present is at least two of the following: poor appetite or overeating, insomnia or hypersomnia, low energy or fatigue, low self-esteem, poor concentration or difficulty making decisions or feeling of hopelessness. These symptoms are not superimposed on a chronic psychotic disorder such as schizophrenia or delusional disorder. Also it cannot be determined that an organic factor initiated and maintained the disturbance.

There are many ways to show that the composition of the present invention is useful in treating depressive disorders and bipolar disorders such as in animal models. See for example, "Animal Models as Simulations of Depression" by Paul Willner, *TiPS* 12:131–136 (April 1991); "Animal Models of Depression: An overview" by Paul Willner, *Pharmac. Ther.* 45:425–455 (1990), both of which are incorporated herein by reference. One such model is the Chronic Mild Stress Model of Depression ("CMS").

CMS uses mild stressors, such as food and water deprivation, cage tilts, changes of cage mates, etc. Over a period of weeks of exposure to the mild stressors, the animals gradually reduce their consumption of a highly preferred sucrose solution which persists (in untreated animals) for several weeks following the cessation of stress. This decreased sensitivity to reward (the sucrose solution) reflects anhedonia, a symptom of a Major Depressive Episode (see for example, *Behavioral Pharmacol.* 5: Suppl.1, p. 86 (1994) where lithium, carbamazepine and ketoconazole were evaluated in CMS; *Psychopharmacology* 93:358–364 (1987) where a tricyclic antidepressant was evaluated in CMS; *Behavioral Pharmacology:* 5:344–350 (1994) where a catechol-O-methyl transferase inhibitor was evaluated in CMS).

The following CMS study was performed using the Active Ingredient of the compositions of the present invention (hereafter "MDL 100,907") in comparison to known anti-depressant compound Imipramine.

Male Wistar rats were brought into the laboratory two months before the start of the experiment at which time they weighed approximately 300 grams. Except as described below, the animals were singly housed, with food and water freely available, and maintained on a 12 hour light/dark cycle (lights on at 8AM) at a temperature of about 22° C.

The animals were first trained to consume a 1% sucrose solution; training consisted of eight 1 hour baseline tests in which sucrose was presented, in the home cage, following 14 hours food and water deprivation; intake was measured by weighing pre-weighed bottles containing the sucrose solution at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to a chronic mild stress procedure for a period of 9 consecutive weeks. Each week of stress regime consisted of: two periods of food or water deprivation (12 and 14 hour), two periods of 45 degree cage tilt (12 and 14 hour+), two periods of intermittent overnight illumination (lights on and off every 2 hours), two 14 hour periods of soiled cage (200 ml water in sawdust bedding), two 14 hour periods of paired housing, two 14 hour periods of low intensity stroboscopic illumination (150 flashes/min). Stressors were applied continuously throughout the day and night, and scheduled randomly. Control animals were housed in a separate room and had no contract with the stressed animals. They were deprived of food and water for the 14 hours preceding each sucrose test, but otherwise food and water were freely available in the home cage. On the basis of their sucrose intake scores following 3 weeks of stress, both stressed and control animals were each divided further into matched subgroups (n=8), and for subsequent five weeks they received daily administrations of vehicle (1 ml/kg, intraperitoneally (ip)) imipramine (10 mg/kg, ip) or MDL 100,907 (0.002, 0.02 and 0.2 mg/kg orally). All drug injections were in a volume of 1 ml/kg body weight. Drugs were administered at 10AM and sucrose tests were carried out 24 hours following the last drug treatment. After five weeks, the treatments were terminated and after one week of withdrawal a final sucrose test was carried out. Stress was continued throughout the period of treatment and withdrawal.

Results were analyzed by multiple analysis of variance, followed by Fisher's LSD test for post hoc comparisons of means.

Chronic mild stress caused a gradual decrease in the consumption of 1% sucrose solution, in the final baseline test, sucrose intake was approximately 13 gram in both groups. Following three weeks of stress (Week 0), intakes remained at 12.4 ($\pm 0.4$) grams in controls but fell to 7.2 ($\pm 0.2$) grams in stressed animals ($p<0.001$). Such a difference between control and stressed animals treated with vehicle, persisted at similar level for the remainder of the experiment.

Imipramine had no significant effect on the sucrose intake in control animals [$F(1,84)=0.364$; NS]. However, the drug caused a gradual increase of sucrose intake in stressed animals ($F(1,84)=16.776$; $p<0.001$]. Sucrose intake in imipramine-treated stressed animals was significantly increased from Week 0 scores after four weeks of treatment ($p=0.05$) and after five weeks of treatment there were no significant differences between drug-treated stressed animals and drug- and saline-treated controls. The increase of sucrose intake in imipramine-treated stressed animals was maintained at similar level one week after withdrawal from the drug.

MDL 100,907 had no significant effect on the sucrose intake in control animals [Treatment effect: $F(3,168)=0.821$; NS Treatment×Weeks interaction: $F(15,168)=0.499$; NS]. In stressed animals, MDL 100,907 gradually reversed the CMS-induced deficit in sucrose intake, resulting in a significant Treatment effect [$F(3,168)=22.567$; $p<0.001$] and Treatment×Weeks interaction ($F(15,158)=1.559$; $p=0.05$].

In stressed animals treated with two higher doses of MDL 100,907 (0.02 and 0.2 mg/kg), sucrose intakes were significantly increased from initial scores (Week 0) after two (0.02 mg/kg) and three (0.2 mg/kg) weeks of treatment ($p=0.03$ and $p=0.04$, respectively). This effect was increased further during next weeks, and at the end of treatment period (Week 5) the amount of sucrose solution drunk by these animals was comparable to that of vehicle-treated controls and significantly higher than that of vehicle-treated stressed animals (0.02 mg/kg: p<0.001, 0.2 mg/kg: p–0.002).

At the lowest dose of 0.002 mg/kg., MDL 100,907 had no significant effect on the sucrose intake throughout the whole treatment period. In consequence, after five weeks of treatment the sucrose consumption of stressed animals treated with this dose did not differ from the intakes of the vehicle-treated stressed animals (p=0.860) and was significantly lower than the intakes of vehicle-treated controls (p<0.01). One week after withdrawal from the treatment, the sucrose intakes were not significantly changed in all of MDL 100,907-treated control (0.002 mg/kg: p=0.2, 0.02 mg/kg: p=0.9, 0.2 mg/kg: p=0.4) and stressed animals (0.002 mg/kg: p=0.6, 0.02 mg/kg: p=0.8, 0.2 mg/kg: p=0.6).

Of course, clinical trials on humans may also be used to show the usefulness of the compositions of the present invention in treating depression such as using the Abbreviated Hamilton Psychiatric Rating Scale for Depression. This comprises a series of 17 categories in which the individual is rated, e.g., for depressed mood, guilt, suicide tendencies, insomnia, anxiety, etc., to reach a score which indicates to the clinician whether or not the patient is suffering depression.

This invention is further illustrated by the following examples, which are provided for illustration purposes and in no way limit the scope of the present invention.

EXAMPLES (GENERAL)

In the Examples that follow, the following abbreviations are used:

PLGA 50/50—50/50 mole ratio of Poly(DL-lactide-co-glycolide).

DSC—Differential Scanning Calorimetry.

GPC—Gel Permeation Chromatography.

HPLC—High Pressure Liquid Chromatography.

IV—Inherent Viscosity.

MV—Melt Viscosity.

NMR—Nuclear Magnetic Resonance Spectroscopy.

SEM—Scanning Electron Microscopy.

$T_g$—Glass transition temperature.

$T_m$—Melting point—the peak melting temperature.

General Analytical Techniques used for the Characterization: A variety of Analytical techniques were used to characterize the pharmaceutical compositions of the present invention, which included the following:

NMR: NMR analysis was conducted using a 200 MHz spectrometer for the determination of the loading levels of pharmaceutically active compounds, i.e., the drugs used in the present invention. A 500 MHz spectrometer was used for the quantification of transesterification levels. Samples were prepared as 1 weight percent solutions in $CDCl_3$.

DSC: Thermal transitions were measured using a TA Instruments model 3200 calorimeter. Thermal scans from 0 to 200° C. were prepared in a nitrogen atmosphere using a scan rate of 10° C./minute. The DSC curves obtained from the first heating run were taken for analysis.

GPC: Polymer molecular weights were analyzed using a Waters 201 instrument equipped with refractive index. and UV detectors. A solution of 2.0 mg/ml of polymer in THF was prepared for analysis.

HPLC: Drug content was measured by HPLC using a Hewlett-Packard 1090 system. The samples were prepared in an aqueous $CH_3CN$ solution.

IV: The solution viscosity, inherent viscosity, of the polymer samples was measured at 25° C. in a concentration of 0.5 weight percent solution of polymer in chloroform.

MV: The melt viscosity of PLGA was evaluated using a Kayeness capillary rheometer. The rheometer chamber temperature was maintained at 125° C. and viscosity calculations were based on a die measuring 0.6" length and 0.04" diameter.

SEM: Samples for SEM were prepared by freeze fracturing under liquid nitrogen to reveal the internal structure. SEM micrographs of the fractured samples were taken after coating with gold at a magnification of 5,000 to 10,000 X.

Example 1

This Example 1 demonstrates that excellent dispersions of pharmaceutically active molecule in a polymer matrix (i.e., a solid solution) can be obtained by melt mixing in a Haake System 90 melt mixer. The polymer used in this example was PLGA 50/50 having an IV of 0.7 dL/g. The pharmaceutically active molecule used in this example was Compound I, (+)-α-(2,3-dimethoxyphenyl)-1-[2-(4-fluorophenyl)ethyl]-4-piperidinemethanol (Formula I).

The Haake System 90 was equipped with a heated mixing bowl having three zones of temperature control. Contained within the mixing bowl were two counter-rotating mixing blades which draw the fed material into the bowl. The speed (RPM) of the mixing blades was controlled by the operator depending upon the desired level of mixing. The Haake System 90 was also equipped with a computer control unit which regulated the temperature of the bowl and the length of a mixing run.

Since moisture gain was a concern in the storage of the materials, all materials were stored in a freezer with desiccant. All transporting of materials was done in a desiccator. All materials were weighed in a glove box in a dry, nitrogen atmosphere. Once the materials were weighed, their respective jars were sealed, placed into the desiccator and transported into the Haake System 90 melt mixer.

In four separate runs, mixing of PLGA 50/50 with compound of Formula I was carried out as follows. 56 grams of PLGA and 14 grams of Compound I were weighed in a glove box in each of these runs and sealed in separate containers. The Haake melt mixer was heated to the desired temperature, and the mixing blades were set to the desired rotation speed. First, about half of the PLGA polymer was fed into the mixing bowl followed by half of the Compound I. Then the remainder of the PLGA was fed into the mixing bowl followed by the rest of the Compound I. Throughout this feeding step of the materials into the mixing bowl a blanket of nitrogen was maintained over the mixing bowl in order to minimize any degradation of the PLGA polymer due to moisture. Once all of the material had been fed into the mixing bowl, the run timer was started. The run was allowed to go to completion. When the run was completed, the bowl was immediately disassembled and the material was removed using copper knives. The removed. material was placed in a jar and sealed under nitrogen atmosphere. The run number, ratio of PLGA/Compound of Formula I, time needed to completion of mixing, run temperature, and the speed of the blades (RPM) are tabulated in Table I. Also listed in Table I is a control run wherein only PLGA polymer was used in the mixing run.

TABLE 1

| Run Number | Materials | Time | Temperature | RPM |
|---|---|---|---|---|
| Control | 100% PLGA | 3 min | 105° C. | 60 |
| 1 | 80/20 PLGA/Compound of Formula I | 5 min | 105° C. | 60 |
| 2 | 80/20 PLGA/Compound of Formula I | 5 min | 115° C. | 60 |
| 3 | 80/20 PLGA/Compound of Formula I | 4 min | 118° C. | 60 |
| 4 | 80/20 PLGA/Compound of Forrnula I | 5 min | 123° C. | 60 |

The melt blended materials from all of the runs as set forth in Table I were analyzed by DSC. All of the samples from Run Numbers 1 to 4 as set forth in Table I exhibited a single $T_g$ at around 34 to 37° C., whereas the original $T_g$ of the PLGA polymer was around 47° C. This clearly suggests that substantial amounts of the compound of Formula I is dissolved in the PLGA polymer matrix. The DSC analysis also showed a small melting peak due to the melting of the compound of Formula I around 120° C. This melting peak corresponded to the compound of Formula I, which is not dissolved in PLGA. Amounts of compound of Formula I which is not dissolved in PLGA from the Run Numbers 3 to 5 are shown in Table 2. In each of these runs three samples from different areas of the blend was analyzed by DSC.

TABLE 2

| Blend Run Number | Weight percent crystalline drug (undissolved in PLGA) |
|---|---|
| 2 | 2 to 6.5 |
| 3 | 3.5 to 15 |
| 4 | 1.5 to 7 |

The melt blended samples were analyzed by HPLC to determine the amount of compound of Formula I in the sample. The results showed that all of the samples contained 19 weight percent of the compound of Formula I. The samples from run numbers 2 to 4 were further analyzed by SEM. The SEM micrographs showed uniform distribution of the compound of Formula I in the PLGA polymer matrix. The NMR analyses of the blended samples indicated the degree of transesterification was below the quantifiable limits.

Comparative Example 1

This Comparative Example 1 illustrates that dry mixing of the PLGA polymer with compound of Formula I does not afford a miscible blend of the drug molecule in the polymer matrix.

A 20:80 weight ratio of compound of Formula I and PLGA polymer powders were blended together by hand. The blended powders were then analyzed by DSC. The first heating curve showed the $T_m$, the melting peak of the compound of Formula I at 120° C. and the $T_g$ of the polymer at 51° C., as expected. The second heating curve, after cooling from 130° C., showed two separate glass transitions of the drug and polymer at 47° C. and 23° C., respectively. If the two components had formed a miscible blend, only a single $T_g$ is expected. Therefore, this result indicates that the melted drug is not fully dissolved in the polymer melt.

Example 2

This example illustrates the preparation of pharmaceutical compositions containing the biodegradable polymer and a pharmaceutically active molecule using a twin screw extruder.

The melt extrusion experiments in this example was carried out using an 18 mm twin screw extruder, manufactured by Leistritz, which was operated in the co-rotating mode. The polymer used in this example was PLGA 50/50 having an IV of 0.76 dL/g. The pharmaceutically active molecule used in this example was compound of Formula I, (+)-α-(2,3-dimethoxyphenyl)-1-[2-(4-fluorophenyl)ethyl]-4-piperidinemethanol.

The raw materials were metered into the extruder using an Accurate 8000 for PLGA and a K-Tron T-20 for the compound of Formula I. PLGA polymer and the compound were dried for 48 hours under vacuum prior to compounding. The feeders were blanketed with nitrogen during processing to minimize exposure of the raw materials to moisture. The screw was configured to generate a moderate level of mixing without excessive shear. The extrudate exited the die onto a conveyor belt and was allowed to slowly cool before being pelletized in a Conair pelletizer.

The extrudates obtained at various melt temperatures and screw speed were analyzed for weight ratio of PLGA and the compound of Formula I by HPLC and NMR. The extrudate samples obtained at these various conditions were also analyzed for weight average molecular weight ($M_w$), inherent viscosity (IV), thermal transitions, $T_g$ and $T_m$, by DSC and mole percent of transesterification by NMR. The results are summarized in Table 3.

TABLE 3

| Sample No. | Melt temp (° C.) | Screw Speed (rpm) | Mw (g/mol) | Inherent Viscosity | Compound I (wt %) HPLC | Compound I (wt %) NMR | Thermal $T_g$ | Thermal $T_m$ | Transest. (mol %) |
|---|---|---|---|---|---|---|---|---|---|
| 150 | 138 | 200 | 33,000 | 0.40 | 25.0 | 22.6 | 37.3 | 112.9 | 5.1 |
| 160 | 135 | 300 | 31,800 | 0.37 | 15.0 | 15.7 | 36.6 | | 4.7 |
| 170 | 138 | 400 | 32,300 | 0.38 | 22.0 | 22.1 | 36.1 | | 7.4 |
| 180 | 138 | 200 | 34,700 | 0.40 | 14.0 | 15.8 | 41.9 | | 9.5 |
| 190 | 116 | 300 | 42,300 | 0.44 | 11.0 | 14.4 | 40.4 | | 4.7 |
| 200 | 113 | 200 | 44,700 | 0.45 | 10.0 | 7.8 | 43.0 | | 5.5 |

As shown in Table 3, the Tg of the pharmaceutical composition decreases with the increasing weight percent levels of compound of Formula I. This suggests that the compound of Formula I dissolves in the PLGA matrix. This is further confirmed by SEM analyses of these samples, which showed a single phase system.

The extrudate samples were further micronized in a hammer mill. The micronizing was performed under various different process variables, which included the rotor speed (varying from 4500 to 7200 rpm), screen size, and cryogenic conditions. Particle size analysis was conducted either using a Coulter laser analyzer or optical microscopy combined with image analyzer. Various conditions used and the results obtained in these milling experiments are summarized in Table 4.

TABLE 4

| Sample No. | 160 | 170 | 180 |
|---|---|---|---|
| Screen size (in) | 0.020 | 0.012 | 0.012 |
| Rotor speed (rpm) | 6000 | 4500 | 6000 |
| Nitrogen assist | ✓ | ✓ | ✓ |
| Mean particle size (μm) | 196.8 | 223.7 | 230.9 |
| D75 particle size (μm) | 272.6 | 253.2 | 300.7 |
| D10 particle size (μm) | 55.9 | 42.3 | 50.6 |

The milled particles were then classified using stainless steel sieves stacked in a Fritsch vibratory shaker. Samples of particles with a size distribution ranging from 45 microns to 106 microns were separated and tested for the release rate of the compound of Formula I.

Example 3

This example illustrates that lowering of melt temperature, in the extruder lowers the level of transesterification. This example further illustrates that use of compound of Formula I below 20 weight percent in a PLGA matrix results in a composition in which compound of Formula I is totally miscible in the PLGA matrix.

Example 2 was substantially repeated in Example 3 with the exception that the PLGA 50/50 having an IV of 0.44 dL/g was used with the following modifications in the extrusion experiment. A homogeneous dry powder blend of PLGA and the Compound of Formula I in the weight ratio of 85:15 (PLGA:Compound I) was prepared. Prior to dry blending, the Compound I was micronized in a jet mill to a mean particle size of 18 microns. The dry blend of PLGA/Compound I was tumbled for about an hour using a mechanical roller. The dry blend was then dried at room temperature under vacuum for a minimum of about 16 hours.

The dried dry blend was metered into the twin screw extruder using a K-Tron twin screw feeder. The barrel temperatures of the Leistritz twin screw extruder were adjusted to maintain the melt temperatures of the blend between 104° C. and 116° C. Two extrudate samples of the PLGA/Compound I melt blends were prepared at screw speeds of 200 rpm (Sample No. 110) and 150 rpm (Sample No. 120). The samples were analyzed for inherent viscosity, weight percent of Compound I, level of transesterification (mole percent), glass transition temperature ($T_g$, °C.) and the fraction of Compound I, if any. The results are summarized in Table 5.

TABLE 5

| Sample No. | Inherent Viscosity | Weight Percent Compound I | | Trans-esterification (mol %) | Glass transition temp ($T_g$, °C.) | Fraction of crystalline Compound I, % |
|---|---|---|---|---|---|---|
| | | HPLC | NMR | | | |
| 110 | 0.30 | 14.9 | 15.3 | 1.3 | 38.0 | 0 |
| 120 | 0.31 | 15.2 | 14.7 | 1.5 | 39.5 | 0 |

The level of transesterification was quantified by integration of a new peak appearing at 6.0 ppm in the $^1$H NMR spectra. As indicated in Table 5, the level of transesterification is significantly reduced to 1.3 to 1.5 mol percent. Also, as shown in Table 5, there is no crystalline Compound I in the pharmaceutical composition, suggesting that Compound I is totally dissolved in the PLGA polymer matrix.

The extrudates of PLGA/Compound I compositions were milled using a fluidized bed jet mill. The mill used for this purpose was an Alpine AFG100 fluidized bed jet mill. Since micronization in the fluidized bed jet mill occurs by particle-particle contact rather than by impact against a blade, the particles tend to be more spherical. The optical micrographs confirmed the increased spherical shape of jet milled particles relative to the hammer milled particles. A range of conditions was employed to evaluate the effect of classifier speed and grind air pressure on particle size distribution. Table 6 summarizes the milling conditions and resulting particle sizes. Particle sizes were measured using a Coulter LS 230 analyzer in a solution of distilled water and TWEEN 80® surfactant. Samples compounded with lower molecular weight PLGA were micronized to smaller particle sizes due to the more brittle nature of the polymer. The use of the larger diameter nozzles reduced the air pressure in the grind chamber, effecting a larger particle size distribution.

TABLE 6

| Test No. | 1 | 2 | 3 | 4 |
|---|---|---|---|---|
| Material | 110 | 120 | 120 | 120 |
| Nozzle diameter, in. | 1.9 | 1.9 | 3.0 | 3.0 |
| Classifier speed, rpm | 7000 | 4500 | 3000 | 5000 |
| Grind Air pressure, bar | 8 | 8 | 5 | 5 |
| Mean particle size, microns | 23 | 20 | — | 37 |

Example 4

Example 3 was substantially repeated in this example except that the PLGA 54/46 polymer used was of slightly higher molecular weight having an IV of 0.66 dL/g and also contained a residual monomer amount of about 1 mole percent. The pellets of PLGA polymer were milled to a particle size of less than 125 microns using a hammer mill before dry blending with the Compound 1.

Two samples of extrudates of PLGA/Compound I were formed following the procedures of Example 3 at a screw speed of 200 rpm and melt temperatures of 113° C. (Sample No. 210) and 116° C. (Sample No. 2). The samples were analyzed as in Example 3 for inherent viscosity, weight percent of Compound I, level of transesterification (mole percent), glass transition temperature ($T_g$, °C.) and the fraction of Compound I, if any. The results are summarized in Table 7.

TABLE 7

| Sample No. | Inherent Viscosity | Weight Percent Compound I | | Trans-esterification (mol %) | Glass transition temp ($T_g$, °C.) | Fraction of crystalline Compound I, % |
|---|---|---|---|---|---|---|
| | | HPLC | NMR | | | |
| 210 | 0.35 | 15.0 | 15.0 | 3.7 | 35.0 | 0 |
| 220 | 0.38 | 14.1 | 14.9 | 2.6 | 35.0 | 0 |

The milling of the extrudates were carried out as set forth in Example 3. Table 8 summarizes the milling conditions and resulting particle sizes.

TABLE 8

| Test No. | 1 | 2 | 3 |
|---|---|---|---|
| Material | 210 | 210 | 220 |
| Nozzle diameter, in. | 1.9 | 1.9 | 3.0 |
| Classifier speed, rpm | 3900 | 5000 | 5000 |
| Grind Air pressure, bar | 6 | 8 | 8 |
| Mean particle size, microns | 38 | 32 | 38 |

Example 5

This example demonstrates the slow release of the pharmaceutically active compound from the pharmaceutical compositions of the present invention.

Two samples of PLGA/Compound I of Example 1, Run Nos. 2 and 4 were used in this dissolution study. The samples from Example 1, Run Nos. 2 and 4 were milled and sieved to a particle size distribution of 50 to 150 $\mu$m. The dissolution of so formed microparticles was conducted in an USP apparatus #2 at 37° C. using 900 mL of 0.02M phosphate buffer at a pH of about 6.5. 500 mg of microparticles from Example 1, Run Nos. 2 and 4 were used in each of these vessels. The amount of Compound I dissolved in the phosphate buffer was measured by UV spectroscopy at 272 nm. The percent Compound I released was calculated by dividing the Compound I content in solution by the theoretical concentration at 100 percent release based on 20 weight percent loading of Compound I in the microparticles of Example 1. The dissolution profile was followed for 5 days.

The results of dissolution studies are summarized in Table 9.

TABLE 9

| | Percent Compound I Released | |
|---|---|---|
| Time (hours) | Example 1, Run No. 2 | Example I, Run No. 4 |
| 4 | 2 | 2 |
| 24 | 15 | 23 |
| 48 | 28 | 33 |
| 72 | 37 | 40 |
| 96 | 42 | 45 |
| 120 | 46 | 52 |

Example 6

This example 6 illustrates the slow release of the pharmaceutically active compound from the compositions of the present invention at a steady rate over a period of 30 days.

Example 5 was substantially repeated in this example except that the microparticles formed from Example 2, Sample Nos. 170 and 180 were used. The results from the dissolution studies are shown in Table 10.

TABLE 10

| Time | Percent Compound I Released | |
|---|---|---|
| (days) | Example 2, Sample No. 170 | Example 2, Sample No. 180 |
| 0.25 | 14 | 34 |
| 1 | 32 | 44 |
| 2 | 43 | 47 |
| 3 | 61 | 44 |
| 4 | 68 | 47 |
| 5 | 68 | 50 |
| 10 | 73 | 48 |
| 15 | 80 | 58 |
| 20 | 89 | 90 |
| 25 | 97 | 102 |
| 30 | 98 | 104 |

Example 7

This example demonstrates that the release rate of the pharmaceutically active compound depends upon the particle size of the microparticles formed according to the process of the present invention.

Example 5 was substantially repeated in this example except for the following: the microparticles produced from Example 4, Sample No. 210 was used in this example. The extrudates from Example 4, Sample No. 210 was milled and sieved into particles having a size distribution in the range of <37, >37 to <53, >53 to <74, >74 to <150, and >150 microns. These microparticles were then used in the dissolution studies following the procedures as set forth in Example 5. The results from the dissolution studies are shown in Table 11.

TABLE 11

Percent Compound I Released, Microparticles from Example 4, Sample No. 210
Particle Size Dependence

| Time (hours) | >150 $\mu$m | >74 $\mu$m <150 $\mu$m | >53 $\mu$m <74 $\mu$m | >53 $\mu$m <74 $\mu$m | >37 $\mu$m <53 $\mu$m | >37 $\mu$m <53 $\mu$m | >37 $\mu$m <37 $\mu$m |
|---|---|---|---|---|---|---|---|
| 2 | 0 | 2.8 | 3.7 | 5.6 | 13.0 | 15 | 9.4 | 7.2 |
| 4 | 0 | 3.1 | 5.5 | 11.5 | 21.5 | 18.7 | 14.2 | 14.4 |
| 21 | 7.3 | 10.5 | 15.9 | 21.2 | 28.3 | 33 | 28.9 | 33.7 |
| 50 | 9.7 | 19.0 | 21.5 | 28.2 | 32.9 | 38.4 | 38.4 | 43.9 |
| 119 | 49.3 | 53.5 | 45.6 | 53.3 | 59.0 | 61.1 | 65.1 | 55.1 |
| 122 | 45.8 | 49.2 | 42.2 | 50.5 | 50.2 | 57.3 | 65.4 | 66.5 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method for the production of a pharmaceutical composition comprising the steps of:
   a) mixing a suitable amount of pharmaceutically active compound of Formula I:

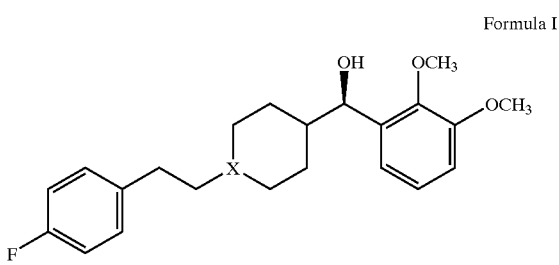

Formula I or a pharmaceutically acceptable salt thereof with a suitable amount of biodegradable polymer for a sufficient period of time and at suitable temperature and pressure conditions to form a dry mixture of said pharmaceutically active compound and said polymer, wherein said biodegradable polymer has a glass transition temperature ($T_g$) of less than about 60° C.;
   b) subjecting said dry mixture to a suitable shear mixing using a single screw extruder under suitable temperature and pressure conditions for a sufficient period of time such that said polymer softens to form a fluidized medium and said pharmaceutically active compound is sufficiently dissolved to form a solid solution having substantially homogeneously dispersed mixture of said pharmaceutically active compound and said polymer, and said homogeneous mixture is formed into a strand;
   c) pelletizing said strand; and
   d) pulverizing said pellets to form sustained release microparticles of said biodegradable polymer and said pharmaceutically active compound, wherein said microparticles are having a size distribution in the range of from about 10 to 200 μm such that said microparticles are suitable for forming an injectable formulation.

2. The method as set forth in claim 1 wherein said polymer is selected from the group consisting of polyester, polyamide, polyanhydrides, polyorthoesters, polycarbonates, poly(phosphoesters), poly(phosphazenes), poly(iminocarbonates), and mixtures thereof.

3. The method as set forth in claim 1 wherein said polymer is selected from the group consisting of polylactide, polyglycolide, polylactide-co-glycolide, polyhydroxybutyrate, polycaprolactone, polytartarate, and mixtures thereof.

4. The method as set forth in claim 1 wherein said polymer is polylactide-co-glycolide.

5. The method as set forth in claim 4 wherein said polylactide-co-glycolide has a weight average molecular weight of from about 20,000 to about 100,000.

6. The method as set forth in claim 4 wherein said polylactide-co-glycolide has a weight average molecular weight of from about 30,000 to about 45,000.

7. The method as set forth in claim 4 wherein said polylactide-co-glycolide contains 45 to 90 mole percent of lactide and 10 to 55 mole percent of glycolide units respectively.

8. The method as set forth in claim 1 wherein said mixing in step (a) is carried out at ambient temperature.

9. The method as set forth in claim 1 wherein said mixing in step (a) is carried out at a temperature in the range of from about 20° C. to about 30° C.

10. The method as set forth in claim 1 wherein said shear mixing in step (b) is carried out using a twin screw extruder.

11. The method as set forth in claim 1 wherein said shear mixing in step (b) is carried out at a temperature in the range of from about 60° C. to about 140° C.

12. The method as set forth in claim 1 wherein said shear mixing in step (b) is carried out at a temperature in the range of from about 80° C. to about 120° C.

13. The method as set forth in claim 1 wherein said shear mixing in step (b) is carried out at a temperature in the range of from about 95° C. to about 115° C.

14. The method as set forth in claim 1 wherein weight ratio of said pharmaceutically active compound to said polymer is in the range of from about 5:95 to about 25:75.

15. The method as set forth in claim 1 wherein weight ratio of said pharmaceutically active compound to said polymer is in the range of from about 10:90 to about 20:80.

16. The method as set forth in claims 1 wherein said pharmaceutically active compound is dissolved in said polymer at least to an extent of about 50 weight percent based on the total weight of said pharmaceutically active compound present in said composition.

17. The method as set forth in claim 1 wherein said pharmaceutically active compound is dissolved in said polymer at least to an extent of about 90 weight percent based on the total weight of said pharmaceutically active compound present in said composition.

18. The method as set forth in claim 1 wherein said microparticles are added to a pharmaceutically acceptable solution to form an injectable suspension.

19. The method as set forth in claim 18 wherein said suspension when administered to a patient releases said pharmaceutically active molecule for a period of at least about 2 weeks at a dose sufficient to antagonize the effects of serotonin at the $5HT_{2A}$ receptor.

20. The method as set forth in claim 18 wherein said suspension when administered to a patient releases said pharmaceutically active molecule for a period of from about 2 weeks to about one month at a dose sufficient to antagonize the effects of serotonin at the $5HT_{2A}$ receptor.

21. A method for the preparation of a pharmaceutical composition comprising the steps of:
   a) mixing a pharmaceutically active compound of Formula I

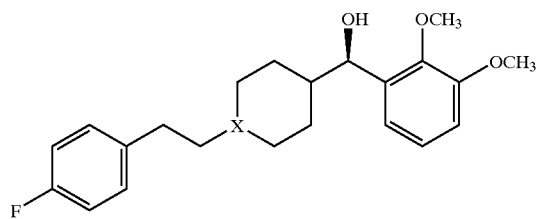

Formula I or a pharmaceutically acceptable salt thereof and a polylactide-co-glycolide polymer at a temperature of about 25° C. and atmospheric pressure conditions for a sufficient period of time to form a mixture of said compound and said polymer, wherein weight ratio of said compound to said polymer is in the range of from about 10:90 to about 15:85, and wherein said polymer has a glass transition temperature ($T_g$) of less than about 60° C.;

b) drying said mixture under vacuum at a temperature of about 25° C. for a sufficient period of time such that moisture content of said mixture is less than about 0.02 weight percent;

c) passing said dry mixture through a heated twin screw extruder having at least one left handed element at a sufficient shear rate and at temperature of from about 95° C. to 115° C. for a sufficient period of time such that said polymer is allowed to soften to form a fluidized medium and said compound is allowed to substantially dissolve in said polymer to form a solid solution having a substantially homogeneously dispersed mixture of said compound in said polymer matrix and extruding said homogeneous mixture into a strand, wherein said shearing conditions are maintained in such a way that less than one weight percent of said compound reacts with said polymer;

d) pelletizing said strand; and e) pulverizing and sieving said pellets to form injectable microparticles having a size distribution in the range of from about 10 to 100 μm of the pharmaceutical composition.

22. A pharmaceutical composition consisting essentially of:

microparticles having a size distribution in the range so from about 10 to 100 μm formed of:

a) a biodegradable polymer in an amount of about 80 to 95 percent by weight, wherein said polymer has a glass transition temperature ($T_g$) of less than about 60° C.; and b) a pharmaceutically active compound of Formula I or a pharmaceutically acceptable salt thereof in an amount of about 5 to 20 percent by weight;

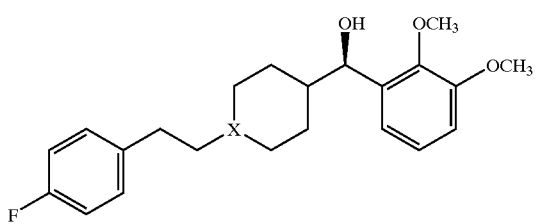

Formula I wherein said compound is a $5HT_{2A}$ receptor antagonist which is substantially dissolved and substantially uniformly dispersed in said polymer.

23. The composition as set forth in claim 22 wherein said polymer is polylactide co-glycolide.

24. The composition as set forth in claim 22 wherein said polylactide-co-glycolide has a weight average molecular weight of from about 20,000 to about 100,000.

25. The composition as set forth in claim 22 wherein said polylactide-co-glycolide has a weight average molecular weight of from about 30,000 to about 45,000.

26. The composition as set forth in claim 22 wherein said polylactide-co-glycolide contains 45 to 90 mole percent of lactide and 10 to 55 mole percent of glycolide units respectively.

27. The composition as set forth in claim 22 wherein said pharmaceutically active molecule is dissolved in said polymer at least to an extent of about 50 weight percent based on the total weight of said pharmaceutically active molecule present in said composition.

28. The composition as set forth in claim 22 wherein said pharmaceutically active molecule is dissolved in said polymer at least to an extent of about 90 weight percent based on the total weight of said pharmaceutically active molecule present in said composition.

29. The composition as set forth in claim 22 wherein said microparticles are added to a pharmaceutically acceptable solution to form an injectable suspension.

30. The composition as set forth in claim 29 wherein said suspension when administered to a patient releases said pharmaceutically active molecule for a period of at least about 2 weeks at a dose sufficient to antagonize the effects of serotonin at the $5HT_{2A}$ receptor.

31. A method for antagonizing the effects of serotonin receptor comprising administering a therapeutically effective amount of a composition according to claim 22 to a patient in need thereof.

32. The method of claim 31 wherein said composition is administered by intramuscular route, and said effects of serotonin receptor are antagonized for a period from about 2 weeks to about one month.

33. A method for antagonizing the effects of serotonin at the $5HT_{2A}$ receptor comprising administering a therapeutically effective amount of a composition according to claim 22 to a patient in need thereof.

34. The method of claim 33 wherein said composition is administered by intramuscular route, and said effects of serotonin at the $5HT_{2A}$ receptor are antagonized for a period from about 2 weeks to about one month.

35. A method of treating a patient for psychoses comprising administering to said patient in need of such therapy a therapeutically effective amount of a composition according to claim 22.

36. The method of claim 35 wherein said composition is administered by intramuscular, intravenous or subcutaneous route.

37. The method of claim 35 wherein said composition is administered by intramuscular route, and said patient is treated for a period from about 2 weeks to about one month.

38. A method of treating a patient for obsessive compulsive disorder comprising administering to said patient a therapeutically effective amount of a composition according to claim 22.

39. A method of treating a patient for drug addiction comprising administering to said patient a therapeutically effective amount of a composition according to claim 22.

40. A method of treating a patient for coronary vasospams comprising administering to said patient a therapeutically effective amount of a composition according to claim 22.

41. A method of treating a patient for angina comprising administering to said patient a therapeutically effective amount of a composition according to claim 22.

42. A method of treating a patient for thrombotic illness comprising administering to said patient a therapeutically effective amount of a composition according to claim 22.

43. A method of treating a patient for sleep disorder comprising administering to said patient a therapeutically effective amount of a composition according to claim 22.

* * * * *